United States Patent

Marzolph et al.

[11] Patent Number: 4,582,849
[45] Date of Patent: Apr. 15, 1986

[54] FUNGICIDAL N-SUBSTITUTED MALEIC ACID IMIDES

[75] Inventors: Gerhard Marzolph, Cologne; Heinz U. Blank, Odenthal; Paul Reinecke, Leverkusen; Wilhelm Brandes, Leichlingen; Hans Scheinpflug, Leverkusen, all of Fed. Rep. of Germany

[73] Assignee: Bayer Aktiengesellschaft, Leverkusen, Fed. Rep. of Germany

[21] Appl. No.: 498,610

[22] Filed: May 27, 1983

[30] Foreign Application Priority Data

Jun. 12, 1982 [DE] Fed. Rep. of Germany ....... 3222152

[51] Int. Cl.⁴ ................. C07D 207/452; A61K 31/40
[52] U.S. Cl. .................................... 514/425; 548/548; 548/547; 548/545
[58] Field of Search ............... 548/548, 547, 545; 427/274; 514/425

[56] References Cited

U.S. PATENT DOCUMENTS

| | | | |
|---|---|---|---|
| 2,726,981 | 12/1955 | Wolf et al. | 548/545 |
| 3,129,225 | 4/1964 | Shapiro et al. | 260/247.2 |
| 3,337,584 | 8/1967 | Knock | 548/548 |

FOREIGN PATENT DOCUMENTS

| | | | |
|---|---|---|---|
| 0045907 | 2/1982 | European Pat. Off. | |
| 1695306 | 3/1971 | Fed. Rep. of Germany | |
| 0122065 | 7/1982 | Japan | 548/547 |
| 880555 | 10/1961 | United Kingdom | |

*Primary Examiner*—Glennon H. Hollrah
*Assistant Examiner*—D. B. Springer
*Attorney, Agent, or Firm*—Sprung Horn Kramer & Woods

[57] ABSTRACT

Fungicidally active substituted maleic acid amides of the formula

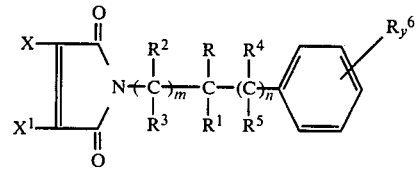

in which
X is hydrogen, chlorine or bromine,
$X^1$ is chlorine or bromine,
R is alkyl, optionally substituted aryl or optionally substituted aralkyl,
$R^1$ to $R^5$ each independently is hydrogen, alkyl, optionally substituted aryl or optionally substituted aralkyl,
$R^6$ each independently is halogen, alkyl, optionally substituted aryl, optionally substituted cycloalkyl, alkoxy, sulphonylamine, halogenoalkyl, nitro, cyano, alkoxycarbonyl, alkylsulphonyl or carboxylamine,
n is 0, 1, 2 or 3,
m is 0, 1, 2 or 3,
m+n is 0, 1, 2 or 3, and
y is 0, 1, 2, 3, 4 or 5,
with the exception of the compound in which
X and $X^1$ are chlorine,
m and y are 0,
n is 1,
$R^1$, $R^4$ and $R^5$ are hydrogen, and
R is methyl,
and the compound in which
X and $X^1$ are chlorine,
m, n and y are 0,
$R^1$ is hydrogen, and
R is phenyl.

10 Claims, No Drawings

FUNGICIDAL N-SUBSTITUTED MALEIC ACID IMIDES

The present invention relates to new substituted maleic acid imides, several processes for their preparation and their use as agents for combating pests.

It is already known that N-sulphenylated dicarboxylic acid imides, such as, for example, N-trichloromethylthio-tetrahydrophthalimide, has a fungicidal activity (compare U.S. Pat. No. 2,553,770).

It is also known that N-benzylmaleic acid imides, for example N-(2'-methylbenzyl)-3,4-dichloro-maleic acid imide, have fungicidal properties (compare Japanese Patent Application No. 52-93,765).

N-Aralkyl-maleic acid imides, such as N-(1-methyl-2-phenyl-ethyl)-3,4-dichloromaleic acid imide and N-(1,1-diphenylmethyl)-3,4-dichloromaleic acid imide are also known (compare U.S. Pat. No. 3,129,225). Nothing is known of their use as agents for combating pests.

New substituted maleic acid imides of the formula (I)

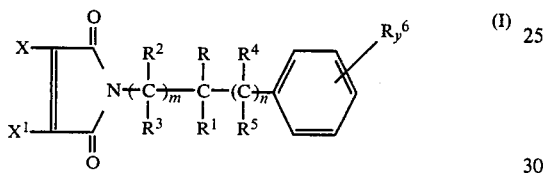

in which
X represents hydrogen, chlorine or bromine,
$X^1$ represents chlorine or bromine,
R represents alkyl, optionally substituted aryl or optionally substituted aralkyl,
$R^1$ to $R^5$ are identical or different and represent hydrogen, alkyl, optionally substituted aryl or optionally substituted aralkyl,
$R^6$ represents halogen, alkyl, optionally substituted aryl, optionally substituted cycloalkyl, alkoxy, sulphonylamine, halogenoalkyl, nitro, cyano, alkoxycarbonyl, alkylcarbonyl, alkylsulphonyl or carboxylamine,
n represents 0, 1, 2 or 3 and
m represents 0, 1, 2 or 3, and the sum of n and m is not greater than 3, and, if n and m is greater O, $R^2$, $R^3$, $R^4$ and $R^5$ can in each case represent several identical or different radicals, and
Y represents 0, 1, 2, 3, 4 or 5, and, if Y is greater than 1, the substituents can be identical or different,
with the exception of the compounds in which
X and $X^1$ represent chlorine,
m and y represent 0,
n represents 1,
$R^1$, $R^4$ and $R^5$ represent hydrogen and
R represents methyl,
and in which
X and $X^1$ represent chlorine,
m, n and y represent 0,
$R^1$ represents hydrogen and
R represents phenyl,
have now been found.

The compounds of the formula (I) can be in the form of an isomer mixture or in the form of the individual optical antipodes.

It has furthermore been found that the substituted maleic acid imides of the formula (I)

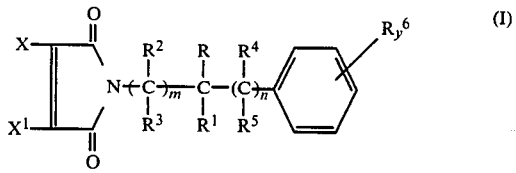

in which
X represents hydrogen, chlorine or bromine,
$X^1$ represents chlorine or bromine,
R represents alkyl, optionally substituted aryl, or optionally substituted aralkyl,
$R^1$ to $R^5$ are identical or different and represent hydrogen, alkyl, optionally substituted aryl or optionally substituted aralkyl,
$R^6$ represents halogen, alkyl, optionally substituted aryl, optionally substituted cycloalkyl, alkoxy, sulphonylamine, halogenoalkyl, nitro, cyano, alkoxycarbonyl, alkylcarbonyl, alkylsulphonyl or carboxylamine,
n represents 0, 1, 2 or 3 and
m represents 0, 1, 2 or 3, and the sum of n and m is not greater than 3, and, if n and m is greater O, $R^2$, $R^3$, $R^4$ and $R^5$ can in each case represent several identical or different radicals, and
y represents 0, 1, 2, 3, 4 or 5, and, if y is greater than 1, the substituents can be identical or different,
are obtained by a process in which
(a) a halogenomaleic acid anhydride of the formula (II)

in which
X and $X^1$ have the abovementioned meanings, is reacted with primary amines of the formula (III)

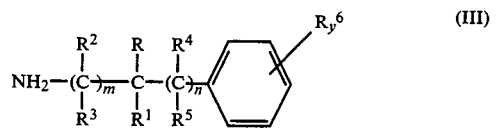

in which
R to $R^6$, m, n and y have the abovementioned meanings,
in a diluent, or
(b) a halogenomaleic acid dialkyl ester of the formula (IV)

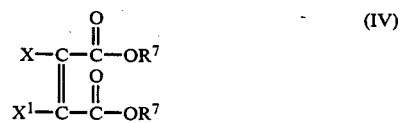

in which
X and $X^1$ have the abovementioned meanings
$R^7$ represents alkyl, is reacted with primary amines of the formula (III) in which R to $R^6$, m, n and y have the abovementioned meanings, if appropriate in a solvent or diluent, or
(c) halogenomaleic acid monoamides of the formula (V)

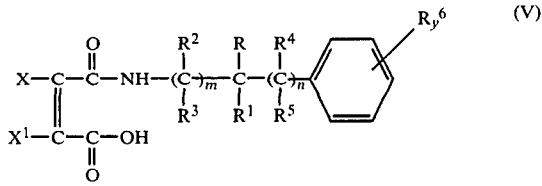

in which
X, $X^1$, R to $R^6$, m, n and y have the abovementioned meanings,
are cyclized in the presence of a solvent, such as, for example, glacial acetic acid and, if appropriate, an anhydridizing agent, such as, for example, acetic anhydride or thionyl chloride, to give the compounds of the formula (I).

The new substituted maleic acid imides have powerful fungicidal properties. Surprisingly, the compounds of the formula (I) according to the invention display a considerably more powerful action than the compounds which are known from the prior art and are closely related compounds from the point of view of their action.

The invention preferably relates to those substituted maleic acid imides of the formula (I) in which
X represents chlorine or bromine,
$X^1$ represents chlorine or bromine,
R represents straight-chain or branched alkyl with 1 to 6 carbon atoms, aryl which is optionally mono-, di-, tri-, tetra- or penta-substituted by identical or different alkyl or halogen groups, or aralkyl which is optionally mono-, di-, tri-, tetra- or penta-substituted by identical or different alkyl, halogenoalkyl or halogen groups in the aryl part,
$R^1$ to $R^5$ are identical or different and represent hydrogen, straight-chain or branched alkyl with 1 to 6 carbon atoms, aryl which is optionally mono-, di-, tri-, tetra- or penta-substituted by identical or different alkyl, halogenoalkyl or halogen groups, or aralkyl which is optionally mono-, di-, tri-, tetra- or penta-substituted by identical or different halogen, alkyl or halogenoalkyl groups in the aryl part,
$R^6$ represents halogen, alkyl with 1 to 6 carbon atoms, aryl or cycloalkyl which is optionally mono-, di-, tri-, tetra- or penta-substituted by identical or different halogen or alkyl groups, alkoxy with 1 to 4 carbon atoms, sulphonylamine, nitro, cyano, halogenoalkyl with 1 to 5 halogen and 1 to 6 carbon atoms, alkoxycarbonyl, alkylcarbonyl or alkylsulphonyl with 1 to 4 carbon atoms in each alkyl radical, or carboxylamine,
m and n represent 0, 1, 2 or 3,
the sum of n and m is preferably 0, 1 or 2 and
y represents 0, 1, 2 or 3,
with the exception of the compounds in which
X and $X^1$ represent chlorine,
m and y represent 0,
n represents 1,
$R^1$-$R^4$ and $R^5$ represent hydrogen and
R represents methyl,
and those wherein
X and $X^1$ represent chlorine,
m, n and y represent 0,
$R^1$ represents hydrogen and
R represents phenyl.

Particularly preferred substituted maleic acid imides of the formula (I) are those in which
X and $X^1$ represent chlorine,
R represents straight-chain or branched alkyl with 1 to 4 carbon atoms, such as methyl, ethyl, n-propyl, iso-propyl, n-butyl, sec.-butyl, isobutyl and tert.-butyl, or phenyl, benzyl or phenethyl which is optionally mono-, di- or tri-substituted by identical or different radicals from the group comprising methyl, ethyl, chlorine and bromine,
$R^1$ to $R^5$ are identical or different and represent hydrogen, straight-chain or branched alkyl with 1 to 4 carbon atoms, such as methyl, ethyl, n-propyl, iso-propyl, n-butyl, iso-butyl, sec.-butyl and tert.-butyl, or phenyl, benzyl or phenethyl which is optionally mono-, di- or tri-substituted by identical or different radicals from the group comprising methyl, ethyl and chlorine,
$R^6$ represents chlorine, bromine, alkyl with 1 to 4 carbon atoms, such as methyl, ethyl, n-propyl, iso-propyl, n-butyl, sec.-butyl, iso-butyl or tert.-butyl, alkoxy with 1 to 3 carbon atoms, such as methoxy, ethoxy, n-propoxy or iso-propoxy, sulphonylamine, alkylsulphonyl or alkylcarbonyl with 1 to 3 carbon atoms in the alkyl part, such as methylsulphonyl, ethylsulphonyl, n-propylsulphonyl, iso-propylsulphonyl, methylcarbonyl, ethylcarbonyl, n-propylcarbonyl or isopropylcarbonyl, carbonylamine, trifluoromethyl, phenyl, cyclopentyl, cyclohexyl or alkoxycarbonyl with 1 to 3 carbon atoms in the alkoxy part, such as methoxycarbonyl, ethoxycarbonyl, n-propoxycarbonyl or iso-propoxycarbonyl,
m and n represent 0, 1, 2 or 3,
the sum of n and m represents 0, 1 or 2 and
y represents 0, 1, 2 or 3,
with the exception of those compounds in which
X and $X^1$ represent chlorine,
m and Y represent 0,
n represents 1,
$R^1$, $R^4$ and $R^5$ represent hydrogen and
R represents methyl,
and those wherein
X and $X^1$ represent chlorine,
m, n and y represent 0,
$R^1$ represents hydrogen and
R represents phenyl.

If, for example, dibromomaleic anhydride and 3-phenyl-1,2,3,3-tetramethylpropylamine are used for process variant (a), the course of the reaction can be represented by the following equation:

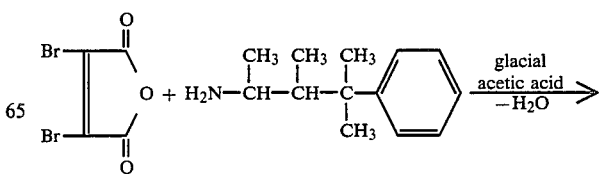

-continued

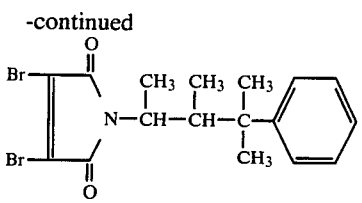

If dimethyl dichloromaleate and 2-phenyl-1,2-dimethylethylamine are used as starting substances in process variant (b), the course of the reaction can be represented by the following equation:

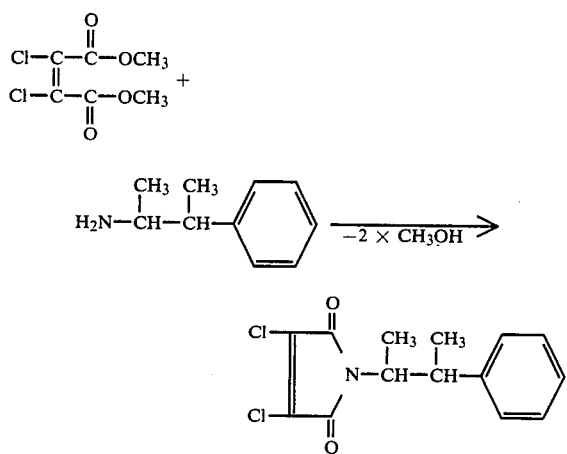

If dichloromaleic anhydride and 1,1-dimethyl-2-phenyl-ethylamine are used as starting substances in process variant (c), the dichloromaleic acid monoamides are obtained, and are cyclized. The course of this reaction can be represented by the following equation:

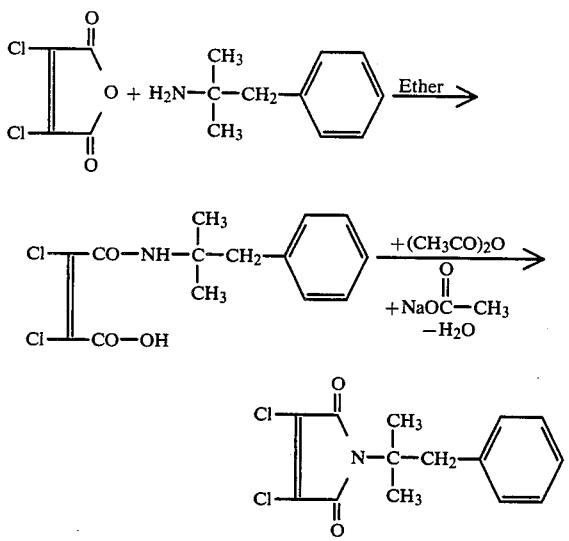

Formula (II) provides a general definition of the halogenomaleic anhydrides required as starting compounds in carrying out process variant (a). These compounds are commercially available and/or can easily be prepared by known processes. The amines also to be used in process variants (a) and (b) are defined by formula (III). In this formula, the radicals have the meanings given already in connection with the description of the substances of the formula (I) according to the invention. Some of the amines are known, or they can be prepared by generally known processes. Thus, the amines can be prepared, for example, by reduction of nitriles or ketoximes with hydrogen (compare Houben-Weyl, Methoden der organischen Chemie [Methods of organic chemistry], XI/1, pages 341 et seq.). Another usual method is reductive amination of aldehydes or ketones with hydrogen or ammonia (compare Houben-Weyl, XI/1, page 341). Above all, the method of amination of halides is suitable for the preparation of aralkylamines (compare Houben-Weyl, volume XI/1, page 24).

The dialkyl halogenomaleates also required in process variant (b) are described by formula (IV). These esters are known and can be obtained by customary processes from commercially available halogenomaleic anhydrides by reaction with alcohols.

Some of the halogenomaleic acid monoamides of the formula (V) to be used in process variant (c) are known, or they can be prepared by processes which are in themselves known, from the corresponding maleic anhydrides by reaction with primary amines (compare Organic Synthesis 41, page 93 (1961)).

Possible diluents for process variant (a) are, above all, carboxylic acids, such as, for example, formic acid, acetic acid and propionic acid.

Possible diluents in process variant (b) are organic solvents. These include, preferably, toluene, xylene, chlorobenzene, perchloroethane, dioxane, glycol dimethyl ether and dimethylformamide.

Diluents which are preferably used in process variant (c) are: carboxylic acids, such as acetic acid; aromatic hydrocarbons, such as toluene or xylene; halogenohydrocarbons, such as chlorobenzene; and also dioxane, and anhydridizing reagents which are preferably used are acetic anhydride, phosgene, thionyl chloride, phosphorus oxychloride or phosphorus pentachloride.

The reaction temperatures can be varied within a substantial range in carrying out the various process variants. Process variant (a) is carried out at temperatures from 20° to 150° C., preferably from 80° to 120° C. Process variant (b) is carried out at temperatures from 50° to 180° C., preferably from 80° to 130° C., and process variant (c) is carried out at temperatures from 0° to 150° C., preferably from 50° to 120° C.

In general, all three variants are carried out under normal pressure.

In carrying out all process variants, the starting substances are preferably used in equimolar amounts.

According to a preferred embodiment of process variant (a), equimolar amounts of the starting substances are stirred in an organic solvent, for example glacial acetic acid, at elevated temperature for several hours. The mixture is then cooled to room temperature, and water is added, the product already being separated out.

If dibromomaleic anhydride is used as the starting substance, this is prepared, in a preferred embodiment, in a solution of dibromomaleic acid in glacial acetic acid, while stirring, and is further reacted directly with the amine in this solution.

According to a preferred embodiment of process variant (b), the dialkyl dihalogenomaleate is prepared from the dihalogenomaleic anhydride and methanol, and is reacted with the amine, after fractional distillation. Working up is carried out as described above (compare U.S. Pat. No. 3,734,927, Example 5).

The active compounds according to the invention exhibit a powerful microbicdal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

When used in appropriate concentrations, the compounds also have an acaricidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate can be used in the formulations.

It is possible to use colorants such as inorganic pigments, for example iron oxide, titanium oxide and Prussian Blue, and organic dyestuffs, such alizarin, azo and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

Example 1

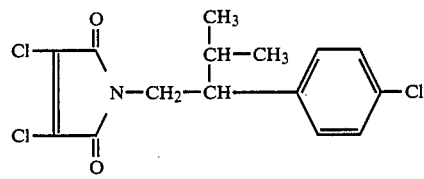

16.7 g (0.1 mol) of dichloromaleic anhydride and 19.7 g (0.1 mol) of 2-(4-chlorophenyl)-3-methylbutylamine are stirred in 100 ml glacial acetic acid at 120° C. for 4 hours. The mixture is cooled to 20° C. and 10 ml of water are added. A colorless precipitate separates out, and is filtered off with suction and dried. 21.2 g of dichloromaleic acid N-[2-(4-chlorophenyl)-3-methylbutyl]imide of melting point 91°–92° C. are obtained. A further 10.4 g of imide can also be isolated by stirring the mother liquor with water. The total yield is: 91.3% of theory.

Example 2

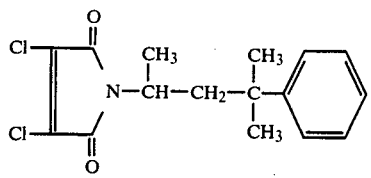

16.7 g (0.1 mol) of dichloromaleic anhydride and 17.7 g (0.01 mol) of 3-phenyl-1,3,3-trimethylpropylamine are stirred in 100 ml of glacial acetic acid under reflux for 4 hours. 50 ml of water are added and the mixture is cooled to 20° C. The product is filtered off with suction and dried. 23.5 g (72% of theory) of dichloromaleic acid N-(3-phenyl-1,3,3-trimethylpropyl)-imide of melting point 106°–109° C. are obtained.

Example 3

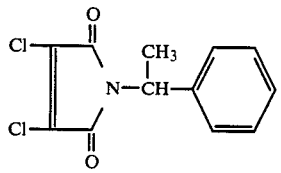

16.7 g (0.1 mol) of dichloromaleic anhydride and 12.0 g (0.1 mol) of α-methylbenzylamine are heated in 100 ml of glacial acetic acid at the boiling point for 4 hours. 100 ml of water are then added and the oil which has separated out is extracted with methylene chloride. The methylene chloride phase is separated off, washed with water, dried and evaporated. The oil which remains cystallizes. 20.8 g (77.3% of theory) of dichloromaleic acid N-1-phenylethylimide of melting point 62°–65° C. are obtained.

Example 4

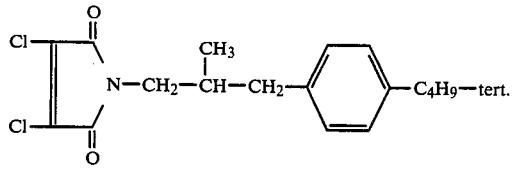

16.7 g (0.1 mol) of dichloromaleic anhydride and 20.5 g (0.1 mol) of 2-methyl-3-(4-tert.-butylphenyl)-propylamine are stirred in 100 ml of glacial acetic acid under reflux for 4 hours. 100 ml of water are added, the oil which has separated out is extracted with methylene chloride, the methylene chloride phase is concentrated and the residue is recrystallized from ethanol. 14.6 g (41.2% of theory) of dichloromaleic acid N-[2-methyl-3-(4-tert.-butylphenyl)-propyl]-imide of melting point 64°–65° C. are obtained.

Example 5

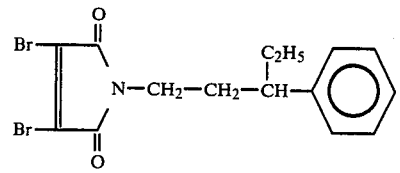

14 g (0.051 mol) of dibromomaleic acid are stirred in 100 ml of glacial acetic acid under reflux for 1 hour. 8.2 g (0.05 mol) of 3-ethyl-3-phenyl-propylamine are added to the cooled solution of the dibromomaleic anhydride thus prepared, and the mixture is stirred under reflux for a further 3 hours. The mixture is cooled to 20° C. and the precipitate is filtered off with suction. After drying, 11.4 g (56% of theory) of dibromomaleic acid N-3-phenylpentylimide of melting point 71°–73° C. are obtained.

The compounds of the formula (I) listed below can be prepared analogously to one of the examples described under 1–5:

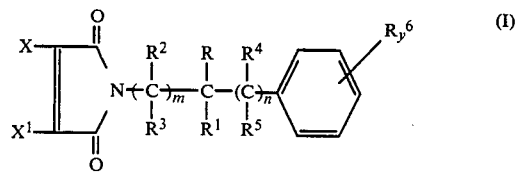

| Example No. | X | $X^1$ | R | $R^1$ | m | $R^2$ | $R^3$ | n | $R^4$ | $R^5$ | $R^6$ | Y | Melting point (°C.) |
|---|---|---|---|---|---|---|---|---|---|---|---|---|---|
| 6 | Cl | Cl | $CH_3$ | H | 1 | H | H | 0 | — | — | — | 0 | 89–90 |
| 7 | Cl | Cl | $CH_3$ | $CH_3$ | 1 | H | H | 0 | — | — | — | 0 | |
| 8 | Cl | Cl | $C_6H_5$ | H | 0 | — | — | 1 | H | H | — | 0 | 88–89 |
| 9 | Cl | Cl | $C_6H_5$ | H | 1 | H | H | 0 | — | — | — | 0 | 132–133 |
| 10 | Cl | Cl | $C_6H_5-CH_2$ | H | 0 | — | — | 1 | H | H | — | 0 | 123–124 |
| 11 | Cl | Cl | $CH_3$ | H | 1 | H | H | 0 | — | — | 2-Cl | 1 | 94–95 |
| 12 | Cl | Cl | $CH_3$ | H | 1 | H | H | 0 | — | — | 4-Cl | 1 | |
| 13 | Cl | Cl | $CH_3$ | $CH_3$ | 1 | H | H | 0 | — | — | 4-Cl | 1 | 98–99 |
| 14 | Cl | Cl | iso-$C_3H_7$ | H | 1 | H | H | 0 | — | — | 4-Cl | 1 | 91–92 |
| 15 | Cl | Cl | $CH_3$ | H | 1 | H | H | 0 | — | — | 2,4-$Cl_2$ | 2 | 118–119 |
| 16 | Cl | Cl | $CH_3$ | H | 1 | H | H | 0 | — | — | 3,4-$Cl_2$ | 2 | |
| 17 | Cl | Cl | $CH_3$ | $CH_3$ | 1 | H | H | 0 | — | — | 3,4-$Cl_2$ | 2 | 98–99 |
| 18 | Cl | Cl | $CH_3$ | H | 1 | H | H | 0 | — | — | 2,6-$Cl_2$ | 2 | 86 |
| 19 | Cl | Cl | $C_6H_5-CH_2-$ | H | 1 | H | H | 0 | — | — | 2,6-$Cl_2$ | 2 | 108–109 |
| 20 | Cl | Cl | $CH_3$ | H | 0 | — | — | 0 | — | — | — | 0 | 62–65 |
| 21 | Cl | Cl | $CH_3$ | H | 0 | — | — | 0 | — | — | 4-$CH_3$ | 1 | 79–80 |
| 22 | Cl | Cl | $CH_3$ | H | 0 | — | — | 0 | — | — | tert.-$C_4H_9$ | 1 | Oil |

-continued

| Example No. | X | X$^1$ | R | R$^1$ | m | R$^2$ | R$^3$ | n | R$^4$ | R$^5$ | R$^6$ | Y | Melting point (°C.) |
|---|---|---|---|---|---|---|---|---|---|---|---|---|---|
| 23 | Cl | Cl | CH$_3$ | H | 1 | H | H | 1 | H | H | — | 0 | 88–89 |
| 24 | Cl | Cl | n-C$_3$H$_7$ | H | 0 | — | — | 0 | — | — | — | 0 | Oil |
| 25 | Cl | Cl | CH$_3$ | H | 1 | H | H | 1 | H | H | 2-Cl | 1 | 98–100 |
| 26 | Cl | Cl | CH$_3$ | H | 0 | — | — | 0 | — | — | 4-Cl | 1 | 101–102 |
| 27 | Cl | Cl | CH$_3$ | H | 0 | — | — | 0 | — | — | 4-OCH$_3$ | 1 | Oil |
| 28 | Cl | Cl | CH$_3$ | H | 0 | — | — | 0 | — | — | 3-CF$_3$ | 1 | |
| 29 | Cl | Cl | CH$_3$ | H | 1 | H | H | 1 | H | H | 4-Cl | 1 | |
| 30 | Cl | Cl | CH$_3$ | H | 1 | H | H | 1 | H | H | 2,4-Cl$_2$ | 2 | 85 |
| 31 | Cl | Cl | CH$_3$ | H | 1 | H | H | 1 | H | H | 3,4-Cl$_2$ | 2 | |
| 32 | Cl | Cl | CH$_3$ | H | 1 | H | H | 1 | H | H | 2,6-Cl$_2$ | 2 | 82–83 |
| 33 | Cl | Cl | CH$_3$ | H | 1 | H | H | 1 | H | H | 4-CH$_3$ | 1 | 99–101 |
| 34 | Cl | Cl | CH$_3$ | H | 1 | H | H | 1 | H | H | 4-OCH$_3$ | 1 | 106–107 |
| 35 | Cl | Cl | CH$_3$ | H | 1 | H | H | 1 | H | H | 4-tert. C$_4$H$_9$ | 1 | 64–65 |
| 36 | Cl | Cl | CH$_3$ | H | 0 | — | — | 2 | H | H | — | 0 | Oil |
| 37 | Cl | Cl | iso-C$_4$H$_9$ | H | 0 | — | — | 2 | H | H | — | 0 | Oil |
| 38 | Cl | Cl | CH$_3$ | H | 0 | — | — | 2 | H | H | 2-Cl | 1 | |
| 39 | Cl | Cl | iso-C$_4$H$_9$ | H | 0 | — | — | 2 | H | H | 2-Cl | 1 | Oil |
| 40 | Cl | Cl | CH$_3$ | H | 0 | — | — | 2 | H | H | 4-Cl | 1 | |
| 41 | Cl | Cl | iso-C$_4$H$_9$ | H | 0 | — | — | 2 | H | H | 4-Cl | 1 | Oil |
| 42 | Cl | Cl | CH$_3$ | H | 0 | — | — | 2 | H | H | 4-CH$_3$ | 1 | Oil |
| 43 | Cl | Cl | CH$_3$ | H | 0 | — | — | 2 | H | H | 3,4-Cl$_2$ | 2 | |
| 44 | Cl | Cl | CH$_3$ | H | 0 | — | — | 2 | H | H | 4-OCH$_3$ | 1 | |
| 45 | Cl | Cl | CH$_3$ | H | 2 | H | H | 0 | — | — | — | 0 | |
| 46 | Cl | Cl | CH$_3$ | H | 2 | H | H | 0 | — | — | 2-Cl | 1 | |
| 47 | Cl | Cl | CH$_3$ | H | 2 | H | H | 0 | — | — | 4-Cl | 1 | |
| 48 | Cl | Cl | CH$_3$ | H | 2 | H | H | 0 | — | — | 3,4-Cl$_2$ | 2 | |
| 49 | Cl | Cl | CH$_3$ | H | 2 | H | H | 0 | — | — | 4-CH$_3$ | 1 | |
| 50 | Cl | Cl | CH$_3$ | H | 2 | H | H | 0 | — | — | 4-OCH$_3$ | 1 | |
| 51 | Cl | Cl | C$_2$H$_5$ | H | 2 | H | H | 0 | — | — | — | 0 | Oil |
| 52 | Cl | Cl | CH$_3$ | H | 1 | CH$_3$ | H | 1 | H | H | — | 0 | Oil |
| 53 | Cl | Cl | CH$_3$ | H | 1 | CH$_3$ | H | 1 | H | H | 3-Cl | 1 | Oil |
| 54 | Cl | Cl | CH$_3$ | H | 0 | — | — | 2 | H CH$_3$ | H & CH$_3$ | — | 0 | 106–109 |
| 55 | Cl | Cl | CH$_3$ | H | 0 | — | — | 2 | H CH$_3$ | H & CH$_3$ | 4-Cl | 1 | 113–114 |
| 56 | Br | Br | CH$_3$ | H | 1 | H | H | 1 | H | H | 4-t-C$_4$H$_9$ | 1 | 118–119 |
| 57 | Br | Br | C$_2$H$_5$ | H | 2 | H | H | 0 | — | — | — | 0 | |
| 58 | Br | Br | i-C$_4$H$_9$ | H | 0 | — | — | 0 | H | H | 2-Cl | 1 | Oil |
| 59 | Br | Br | CH$_3$ | CH$_3$ | 2 | CH$_3$ & H | H H | 0 | — | — | 4-Cl | 1 | 106–108 |
| 60 | Cl | H | CH$_3$ | H | 1 | H | H | 1 | H | H | 3,4-Cl$_2$ | 2 | |
| 61 | Cl | Cl | CH$_3$ | H | 1 | CH$_3$ | H | 1 | CH$_3$ | H | — | 0 | |
| 62 | Cl | Cl | CH$_3$ | H | 1 | H | H | 1 | CH$_3$ | H | — | 0 | |

Use Examples

The compounds shown below are used as comparison substances in the examples which follow:

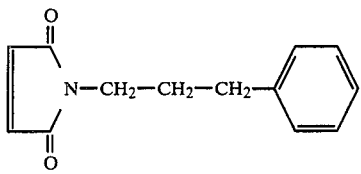
(A)

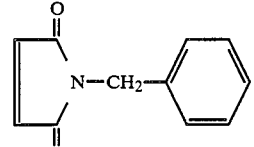
(B)

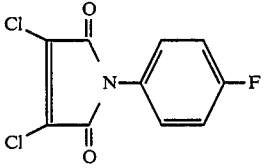
(C)

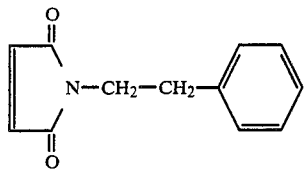
(D)

Example A

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 6 and 4.

Example B

Puccinia test (wheat)/protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 55, 41, 22, 3 and 1.

Example C

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 6, 4, 55, 41, 22 and 53.

Example D

Pyricularia test (rice)/protective

Solvent: 12.5 parts by weight of acetone
Emulsifier: 0.3 part by weight of alkyaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 10 and 14.

Example E

Pyricularia test (rice)/systemic

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compound according to the following preparation example: 4.

Example F

Pellicularia test (rice)

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, a clearly superior activity compared with the prior art is shown, for example, by the compound according to the following preparation example: 55.

It will be appreciated that the instant specification and examples are set forth by way of illustration and not limitation, and that various modifications and changes may be made without departing from the spirit and scope of the present invention.

What is claimed is:

1. A substituted maleic acid of the formula

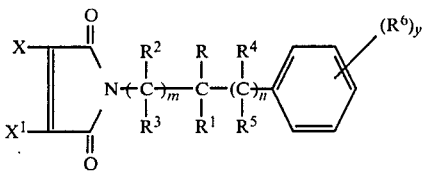

in which

X is hydrogen, chlorine or bromine, $X^1$ is chlorine or bromine,

R is alkyl with 1 to 6 carbon atoms, aryl which is optionally substituted by alkyl and/or halogen groups, or aralkyl which is optionally substituted by alkyl, halogenoalkyl and/or halogen groups in the aryl part, $R^1$ to $R^5$ each independently is hydrogen, alkyl with 1 to 6 carbon atoms, aryl which is optionally substituted by alkyl, halogenoalkyl and/or halogen groups, or aralkyl which is optionally substituted by halogen, alkyl and/or halogenoalkyl groups in the aryl part, $R^6$ each independently is halogen, alkyl with 1 to 6 carbon atoms, aryl or cycloalkyl which is optionally substituted by halogen and/or alkyl groups, alkoxy with 1 to 4 carbon atoms, sulphonylamine, nitro, cyano, halogenoalkyl with 1 to 5 halogen and 1 to 6 carbon atoms, alkoxycarbonyl, alkylcarbonyl or alkylsulphonyl with 1 to 4 carbon atoms in each alkyl radical, or carboxylamine, n is 0, 1 or 2, m is 0, 1 or 2, m+n is 0, 1 or 2, and y is 0, 1, 2, 3, 4 or 5, wherein all aryl radicals are hydrocarbyl aryl, and alkyl not specifically defined as to carbon atoms are lower alkyl, with the exception of the compound in which X and $X^1$ are chlorine, m and y are 0 n is 1, $R^1$, $R^4$ and $R^5$ are hydrogen, and

R is methyl, and the compound in which

X and $X^1$ are chlorine, m, n and y are 0

$R^1$ is hydrogen, and

R is phenyl.

2. A substituted maleic acid imide according to claim 1, in which

X and $X^1$ each independently are chlorine or bromine.

3. A substituted maleic acid imide according to claim 1, in which

X and $X^1$ are chlorine,

R is alkyl with 1 to 4 carbon atoms, or phenyl, benzyl or phenethyl which is optionally mono-, di- or tri-substituted by methyl, ethyl, chlorine and/or bromine, $R^1$ to $R^5$ each independently is hydrogen, alkyl with 1 to 4 carbon atoms, or phenyl, benzyl or phenethyl which is optionally mono-, di or tri-substituted by methyl, ethyl and/or chlorine, $R^6$ each independently is chlorine, bromine, alkyl with 1 to 4 carbon atoms, alkoxy with 1 to 3 carbon atoms, sulphonylamine, alkylsulphonyl, alkoxycarbonyl or alkylcarbonyl with 1 to 3 carbon atoms in the alkyl part, carbonylamine, trifluoromethyl, phenyl, cyclopentyl or cyclohexyl.

4. A substituted maleic acid imide according to claim 1, wherein such imide is dichloromaleic acid N-[2-methyl-3-(4-tert.-butylphenyl)-propyl]-imide of the formula

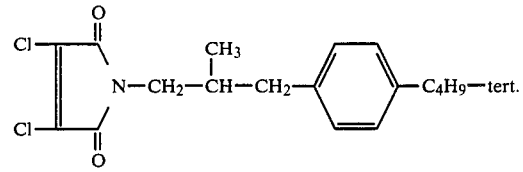

5. A substituted maleic acid imide according to claim 1, wherein such imide is dichloromaleic acid N-[2-(2,6-dichlorophenyl)-propyl]-imide of the formula

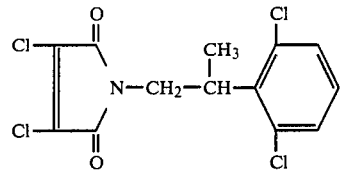

6. A substituted maleic acid imide according to claim 1, wherein such imide is dichloromaleic acid N-(2-benzyl-propyl)-imide, of the formula

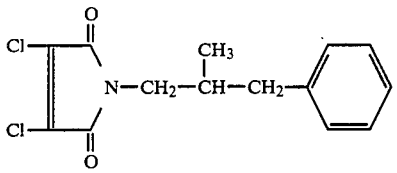

7. A substituted maleic acid imide according to claim 1, wherein such imide is dichloromaleic acid N-[1-(4-chlorophenyl)-ethyl]-imide of the formula

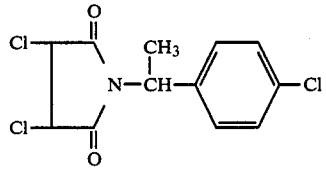

8. A plant pathogen fungicidal composition comprising a fungicidally effective amount of a compound according to claim 1 in admixture with a diluent.

9. A method of combating plant pathogenic fungi which comprises administering to such fungi or to a fungus habitat a fungicically effective amount of a compound according to claim 1.

10. The method according to claim 9, wherein such compound is dichloromaleic acid N-[2-methyl-3-(4-tert.-butyl-phenyl)-propyl]-imide, dichloromaleic acid N-[2-(2,6-dichlorophenyl)-propyl]-imide, dichloromaleic acid N-(2-benzylpropyl)-imide, or dichloromaleic acid N-[1-(4-chlorophenyl)ethyl]-imide.

and it is applied to plant pathogenic fungi or their habitat.

* * * * *